(12) United States Patent
Vahala et al.

(10) Patent No.: US 10,518,108 B2
(45) Date of Patent: Dec. 31, 2019

(54) THERAPY SYSTEM CONTAINING AN MRI MODULE AND MEANS FOR DETERMINING THE POSITION OF AN RF COIL

(71) Applicant: KONINKLIJKE PHILIPS N.V., Eindhoven (NL)

(72) Inventors: Erkki Tapani Vahala, Eindhoven (NL); Wycliffe Adell Raduma, Eindhoven (NL); Tero Jouko Valtter Virta, Eindhoven (NL); Annemaria Johanna Halkola, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 647 days.

(21) Appl. No.: 15/308,858

(22) PCT Filed: Apr. 29, 2015

(86) PCT No.: PCT/EP2015/059259
§ 371 (c)(1),
(2) Date: Nov. 4, 2016

(87) PCT Pub. No.: WO2015/169655
PCT Pub. Date: Nov. 12, 2015

(65) Prior Publication Data
US 2017/0065830 A1 Mar. 9, 2017

(30) Foreign Application Priority Data
May 9, 2014 (EP) ..................................... 14167755

(51) Int. Cl.
*A61B 5/00* (2006.01)
*A61N 5/10* (2006.01)
*A61B 5/055* (2006.01)
*G01R 33/28* (2006.01)
*G01R 33/48* (2006.01)
*A61B 90/00* (2016.01)
*G01R 33/30* (2006.01)

(52) U.S. Cl.
CPC .......... *A61N 5/1039* (2013.01); *A61B 5/0555* (2013.01); *A61B 90/39* (2016.02); *A61N 5/1077* (2013.01); *G01R 33/28* (2013.01); *G01R 33/288* (2013.01); *G01R 33/307* (2013.01); *G01R 33/4808* (2013.01); *A61B 2090/3933* (2016.02); *A61B 2090/3958* (2016.02)

(58) Field of Classification Search
CPC .. A61N 5/1039; A61N 5/1077; G01R 33/307; G01R 33/4808; G01R 33/288; G01R 33/28; A61B 90/39; A61B 5/0555; A61B 2090/3933; A61B 2090/3958
See application file for complete search history.

(56) References Cited

U.S. PATENT DOCUMENTS

| | | | | |
|---|---|---|---|---|
| 8,036,730 | B1 * | 10/2011 | Damadian ............ | A61B 5/0555 324/307 |
| 2008/0221428 | A1 * | 9/2008 | Flask ................... | G01R 33/285 600/410 |
| 2008/0262345 | A1 * | 10/2008 | Fichtinger .............. | A61B 6/504 600/426 |

* cited by examiner

Primary Examiner — Joel Lamprecht

(57) ABSTRACT

The present disclosure relates to a therapy system (100) comprising a radiotherapy device (102) configured to deliver and direct a radiotherapy beam along an axis to a predefined target position (117) in an imagine zone (138, 146) within an MR module (106) of the therapy system (100). The predefined target position (117) is matched with a position of an RF coil (140) of the MR module (106).

15 Claims, 2 Drawing Sheets

THERAPY SYSTEM CONTAINING AN MRI MODULE AND MEANS FOR DETERMINING THE POSITION OF AN RF COIL

CROSS REFERENCE TO RELATED APPLICATIONS

This application is a U.S. national phase application of International Application No. PCT/EP2015/059259, filed on Apr. 29, 2015, which claims the benefit of EP Application Serial No. 14167755.9 filed on May 9, 2014 and is incorporated herein by reference.

TECHNICAL FIELD OF THE INVENTION

The invention relates to energy treating devices, in particular to the use of a therapy system for applying radiation to a preselected anatomical portion of a subject.

BACKGROUND OF THE INVENTION

Integrated magnetic resonance imaging (MRI) and Linear Accelerators (LINAC) system image guidance during radiotherapy has become increasingly important and has gained wide application during the last years. The aim of the system is to deliver a precise radiation dose to a selected target within the interior of the body based on diagnostic quality MR images. Typically, a LINAC source is placed on a rotating gantry about the magnet of an MRI apparatus and the magnet is designed such that the LINAC rotates in a zero-field region of the magnet.

The target position where the beam is directed at is an essential parameter that affects the tissue destruction along the beam and overall treatment safety. An efficient positioning control and usage of such system may be necessary.

EP 2624915 A1 discloses an image guided radiation therapy system and shielded radiofrequency detector coil for use therein. The international application WO2014/044635 discloses a LINAC guided by a magnetic resonance imaging system. The magnetic resonance imaging system has a radio frequency coil with fiducial markers. These markers are imaged, their position evaluated and position of the radio frequency coil calculated.

SUMMARY OF THE INVENTION

Various embodiments provide for a therapy system, an improved method of operating a medical apparatus, and an improved medical apparatus as described by the subject matter of the independent claims. Advantageous embodiments are described in the dependent claims.

In one aspect, the invention relates to a therapy system comprising a magnetic resonance module comprising a main magnet and a patient carrier configured to move into or out of an examination zone within the main magnet; a radiotherapy device configured to deliver and direct a radiotherapy beam along an axis to a predefined target position in the imagine zone; a RF coil connected to the patient carrier, wherein the RF coil is provided with a plurality of fiducial markers that are configured for emitting magnetic resonance signals; a positioning system for positioning the patient carrier; a spoiler; a memory for storing machine executable instructions; and a processor, wherein execution of the machine executable instructions causes the processor to:

a. control the positioning system to move the patient carrier;
b. control the MRI module to acquire MRI data responsive to excitation of magnetic resonance in at least a first set of the plurality of fiducial markers;
c. reconstruct using the MRI data an image representation of the first set of fiducial markers;
d. calculate the position of the RF coil using the position of the first set of fiducial markers in the reconstructed image;
e. control the spoiler to suppress magnetic resonance signals emitted from one or more fiducial markers of the first set of fiducial markers based on the calculated position;
f. repeating steps a)-e) using a second set of fiducial markers of the plurality of the fiducial markers as the first set of fiducial markers until the calculated position matches the predefined target position, wherein the second set of the fiducial markers comprises at least the first set of fiducial markers.

The second set of fiducial markers may comprise at least the first set of fiducial markers excluding zero or more fiducial markers of the one or more fiducial markers. In addition, the second set of fiducial markers may further comprise one or more fiducial markers of the plurality of fiducial markers that are not part of the first set of fiducial markers. The RF coil may be a transmitter and/or a receiver coil.

For example, in case the plurality of fiducial markers may be deactivated (disabled or switched off), step a) further comprises activating (enabling or switching on) the first set of fiducial markers. An activated (deactivated) fiducial marker may (may not) emit coherent magnetic resonance signals (e.g. the RF coil may still receive from deactivated fiducial markers no signal or a weak signal, but the signal is minimal/incoherent e.g. due to spoiling and thus may add a bit of noise) in response to RF excitations. The fiducial markers may also be embedded into a holder of the RF coil.

The spoiler may be a control unit of the MRI module, for example, an electronic switch as a diode switching circuit connected to at least the RF coil to control the RF coil e.g. for shifting the resonance frequency of the RF coil, and/or to control a gradient coil to shift or switch on and off a gradient field e.g. slice selection gradient field.

The spoiler may be a control unit of the MRI module that controls the RF coil and/or the gradient coil to perform the RF spoiling and/or the gradient spoiling respectively. The RF spoiling and the gradient spoiling may be used such that signals are not emitted from the fiducial markers or that the signals emitted from the fiducial markers are not (cannot be) coherently received by the RF coil.

In another example, the spoiler may wrap around each of the plurality of the markers. It may be for example a miniature solenoid coil around the fiducial marker e.g. having a spherical shape.

The plurality of fiducial markers may include dipoles having a first resonance frequency different from a proton resonance frequency. The excitation of magnetic resonance may comprise exciting magnetic resonance in dipoles of the first set of fiducial markers. The excitation may further comprise exciting dipoles in a target volume of the patient (e.g. a target volume close to the fiducial markers), wherein the excitation of both dipoles may be concurrently performed with common or separate radio frequency pulses. The dipoles in the target volume have a second resonance frequency that is the proton resonance frequency. This may be beneficial, as the fiducial marker RF pulses do not interfere with the spin excitation of the target volume and fiducial marker signal does not eclipse valuable morphological information from the patient.

According to one embodiment, the execution of the machine executable instructions further causes the processor to control the radiotherapy device to deliver energy to a target volume at the predefined target position using acquired MRI data with the RF coil being at the calculated position that matches the target position.

According to one embodiment, the execution of the machine executable instructions further causes the processor to move the radiotherapy device for delivering energy to the target volume at a second predefined target position, and repeat steps a)-f) for the second predefined target position.

These features may provide an accurate and reliable therapy procedure and/or planning as it is guided with an accurate imaging process using an accurately positioned RF coil. The images that are used to guide the radiotherapy device accurately reflect the position of the target volume that it is radiated by the radiotherapy device.

The suppression of signals of at least part of the fiducial markers may reduce the artifacts in the reconstructed images which may in turn increase the accuracy of the RF coil positioning compared to the case where signals of all initial markers are not suppressed until the end of the RF coil positioning, and more importantly, allow turning off (or suppressing of signals from the fiducial markers) of the markers altogether when performing imaging during radiation therapy. This is beneficial, as the suppressed fiducial marker signals may not confound automatic tissue motion detection algorithms, which could be the case if the markers were visible or if marker signal was allowed to alias over the tissue signal in the images.

According to one embodiment, matching the calculated position with the target position in step f) comprises comparing the distance between the calculated position and the target position with a predefined minimum matching distance threshold value; in response to a determination that the distance is smaller than the predefined minimum matching distance threshold value, determining the radiation level at the calculated position; in response to a determination that the radiation level is higher than a predetermined maximum allowed radiation level, redefining the minimum matching distance threshold value and repeating steps a-e) using the redefined minimum matching distance threshold value.

For example, the radiation level may be defined as a dose rate e.g. having values 0-250 MU/min.

An excessive radiation of the RF coil may induce a radiation induced current (RIC) in the acquired MRI data that may have effect on the MR image signal-to-noise ratio (SNR). This embodiment may provide a balance between an accurate positioning of the RF coil and the protection of the RF coil from excessive radiations. This may further increase the quality of the image produced by the MRI module as it may control a loss in imaging SNR that increases with increasing dose rate. As a result, a further increase in the accuracy/reliability of the therapy procedure may be achieved as the therapy may be based on images for which the SNR due to radiation is under control.

According to one embodiment, the position of the RF coil is calculated in at least one spatial direction, wherein in case the calculated position matches the target position along one spatial direction, suppressing magnetic resonance signals emitted from the fiducial marker used for the calculation of the position along the one spatial direction.

According to one embodiment, in case the calculated position matches the target position, suppressing comprises determining artifact regions in the MRI data and suppressing of magnetic resonance signals emitted from fiducial markers that correspond to the artifact regions.

This embodiment may be advantageous as it may save resources that would otherwise be required to suppress and enable again emission of signals from the fiducial markers that do not induce artifacts on the reconstructed images.

In another aspect, the invention relates to a medical apparatus comprising: a magnetic resonance module comprising a main magnet and a patient carrier configured to move into or out of an examination zone within the main magnet; a RF coil connected to the patient carrier, wherein the RF coil is provided with a plurality of fiducial markers that are configured for emitting magnetic resonance signals; a positioning system for positioning the patient carrier; a spoiler; a memory for storing machine executable instructions; and a processor, wherein execution of the machine executable instructions causes the processor to:
a. control the positioning system to move the patient carrier;
b. control the MRI module to acquire MRI data responsive to excitation of magnetic resonance in at least a first set of the plurality of fiducial markers;
c. reconstruct using the MRI data an image representation of the first set of fiducial markers;
d. calculate the position of the RF coil using the position of the first set of fiducial markers in the reconstructed image;
e. control the spoiler to suppress magnetic resonance signals emitted from one or more fiducial markers of the first set of fiducial markers based on the calculated position;
f. repeating steps a)-e) using a second set of fiducial markers of the plurality of the fiducial markers as the first set of fiducial markers until the calculated position matches a predefined target position, wherein the second set of the fiducial markers comprises at least the first set of fiducial markers.

These features may be advantageous as they may provide an accurate position of the RF coil using the fiducial markers. The intermediate turning off of at least part of the fiducial markers may reduce the artifacts in the intermediate reconstructed images which may in turn increase the accuracy of the RF coil positioning compared to the case where all initial markers are maintained until the end of the RF coil position, and more importantly, allow turning off (or suppressing of signals from the fiducial markers) of the markers altogether when performing imaging e.g. during radiation therapy. This is beneficial, as the suppressed fiducial marker signals may not confound automatic tissue motion detection algorithms, which could be the case if the markers were visible or if marker signal was allowed to alias over the tissue signal in the images. The international application WO2013/011444 mentions an RF surface coil provided with a passive position marker. Fiducial markers coupled with a magnetic resonance receive coil are further mentioned in the international application WO2006/025001.

According to one embodiment, the medical apparatus further comprises a radiotherapy device configured to deliver and direct a radiotherapy beam along an axis to the predefined target position in the imagine zone.

According to one embodiment, matching the calculated position with the target position in step f) comprises: comparing the distance between the calculated position and the target position with a predefined minimum matching distance threshold value; in response to a determination that the distance is smaller than the predefined minimum matching distance threshold value, determining the radiation level at the calculated position; in response to a determination that the radiation level is higher than a predetermined maximum allowed radiation level, redefining the minimum matching distance threshold value and repeating steps a-e) using the redefined minimum matching distance threshold value.

An excessive radiation of the RF coil may induce a radiation induced current (RIC) in the acquired MRI data that may have effect on the MR image signal-to-noise ratio (SNR). This embodiment may provide a balance between an accurate positioning of the RF coil and the protection of the RF coil from excessive radiations. This may further increase the quality of the image produced by the MR module as it may control a loss in imaging SNR that increases with increasing dose rate.

According to one embodiment, step a) further comprises control the positioning system to stop the patient carrier at a predefined stopping time, wherein the repeating of steps a)-e) results in one or more iterations, wherein the predefined stopping time for a given iteration is determined using the calculated position in the previous iteration.

The predefined stopping time for the first iteration is determined using the calculated position in the initial (or first) execution of steps a)-e).

This embodiment may be advantageous as it may allow, for example, accurate and fast deceleration even when marker imaging is carried out with an interval that is not negligible with regards to the patient carrier speed patient carrier position can be extrapolated from the known speed, inertia, and image acquisition time using standard methodology in control theory.

According to one embodiment, repeating of steps a)-e) results in one or more iterations, wherein the MRI module is controlled to acquire the MRI data with an increasing spatial accuracy with the number of iterations.

According to one embodiment, scanning of (e.g. for determining marker positions) marker positions can be interleaved with fast scout imaging. This may be advantageous as it may allow preprocessing of patient data, for example, to automatically position 3D image set over an interesting volume by automatic detection of anatomy landmarks the moment the patient carrier stops at the intended designation. This streamlines the workflow and utilizes the otherwise idle time spent on tabletop movement.

An increase in the spatial resolution may be advantageous as it may allow an accurate calculation of the position of the fiducial markers, in particular, in case the number of markers that emit signals is decreasing with the number of iterations.

According to one embodiment, the fiducial markers include dipoles, wherein suppressing the magnetic resonance signals emitted from the fiducial markers comprises applying at least one of an RF spoiling and gradient spoiling.

An RF spoiling may comprise controlling the phase of the RF pulses such that the RF pulses are transmitted at a specific frequency and phase by the RF coil. The MRI module may be further controlled to receive only signal at that specific phase e.g. transverse magnetization at other phases or positions in the transverse plane are not received by the MRI module. In this case, the specific frequencies and phases may be used to excite dipoles other than dipoles of the fiducial markers.

A gradient spoiling may comprise using the slice select, phase encoding, and frequency encoding gradients to dephase the residual transverse magnetization (RTM), so that it is incoherent at the beginning of the next repetition. For that, a miniaturized coil/current element may be used to create a local inhomogeneity at a fiducial marker.

According to one embodiment, wherein suppressing of the magnetic resonance signals emitted from the fiducial markers comprises de-phasing by the spoiler the dipoles by generating a gradient magnetic field in a region corresponding to the fiducial markers (e.g. for introducing an offset in B0 field that results after the gradient coil fields have been applied). In this case, for example, the spoiler may be a miniaturized coil/current element that may be used to create a local field inhomogeneity (e.g. for shifting B0 field) at the region corresponding to a fiducial marker.

According to one embodiment, the fiducial markers include dipoles having a first resonance frequency, wherein the excitation of magnetic resonance in the fiducial markers is performed using RF excitation pulses generated by the RF coil at least the first resonance frequency, wherein suppressing the magnetic resonance signals emitted from the fiducial markers comprises dynamically varying the frequency (field strength) of the RF excitation pulses for generating RF pulses at a second resonance frequency.

According to one embodiment, the method comprises calculating the position of the RF coil in at least one spatial direction, wherein in case the calculated position matches the target position along one spatial direction, suppressing of magnetic resonance signals emitted from the fiducial marker used for the calculation of the position along the one spatial direction.

According to one embodiment, in case the calculated position matches the target position, suppressing comprises determining artifact regions in the MRI data and suppressing emission of magnetic resonance signals from fiducial markers that correspond to the artifact regions.

According to one embodiment, the suppression of the magnetic resonance signals emitted from a fiducial marker is performed if the artifact level of the corresponding artifact region is higher than a predefined artifact level. The artifact level may be determined by evaluating image metrics of reconstructed images. The image metric may be obtained for example, by measuring the highest SNR with small amount of filtering within the area indicated, by marker shape cross-correlation, to contain a marker.

In another aspect, the invention relates to a method of controlling a medical apparatus. The medical apparatus comprises: a magnetic resonance module comprising a main magnet and a patient carrier configured to move into or out of an examination zone within the main magnet; a RF coil connected to the patient carrier, wherein the RF coil is provided with a plurality of fiducial markers that are configured for emitting magnetic resonance signals; a positioning system for positioning the patient carrier; and a spoiler. The method comprises:
a. control the positioning system to move the patient carrier;
b. control the MRI module to acquire MRI data responsive to excitation of magnetic resonance in at least a first set of the plurality of fiducial markers;
c. reconstruct using the MRI data an image representation of the first set of fiducial markers;
d. calculate the position of the RF coil using the position of the first set of fiducial markers in the reconstructed image;
e. control the spoiler to suppress magnetic resonance signals emitted from one or more fiducial markers of the first set of fiducial markers based on the calculated position;
f. repeating steps a)-e) using a second set of fiducial markers of the plurality of the fiducial markers as the first set of fiducial markers until the calculated position matches a predefined target position, wherein the second set of the fiducial markers comprises at least the first set of fiducial markers.

In another aspect, the invention relates to a computer program product comprising computer executable instructions to perform the method steps of the above method.

In another aspect, the invention relates to a medical apparatus comprising a magnetic resonance module comprising a main magnet and a patient carrier adapted to move into or out of an examination zone within the main magnet; a RF coil connected to the patient carrier; a positioning system for positioning the patient carrier; a memory for storing machine executable instructions; and a processor, wherein execution of the machine executable instructions causes the processor to:

i. control the positioning system to move the patient carrier;
ii. calculate the position of the RF coil using a video camera of the medical apparatus;
iii. repeating steps i)-ii) until the calculated position matches a predefined target position.

Magnetic resonance image data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
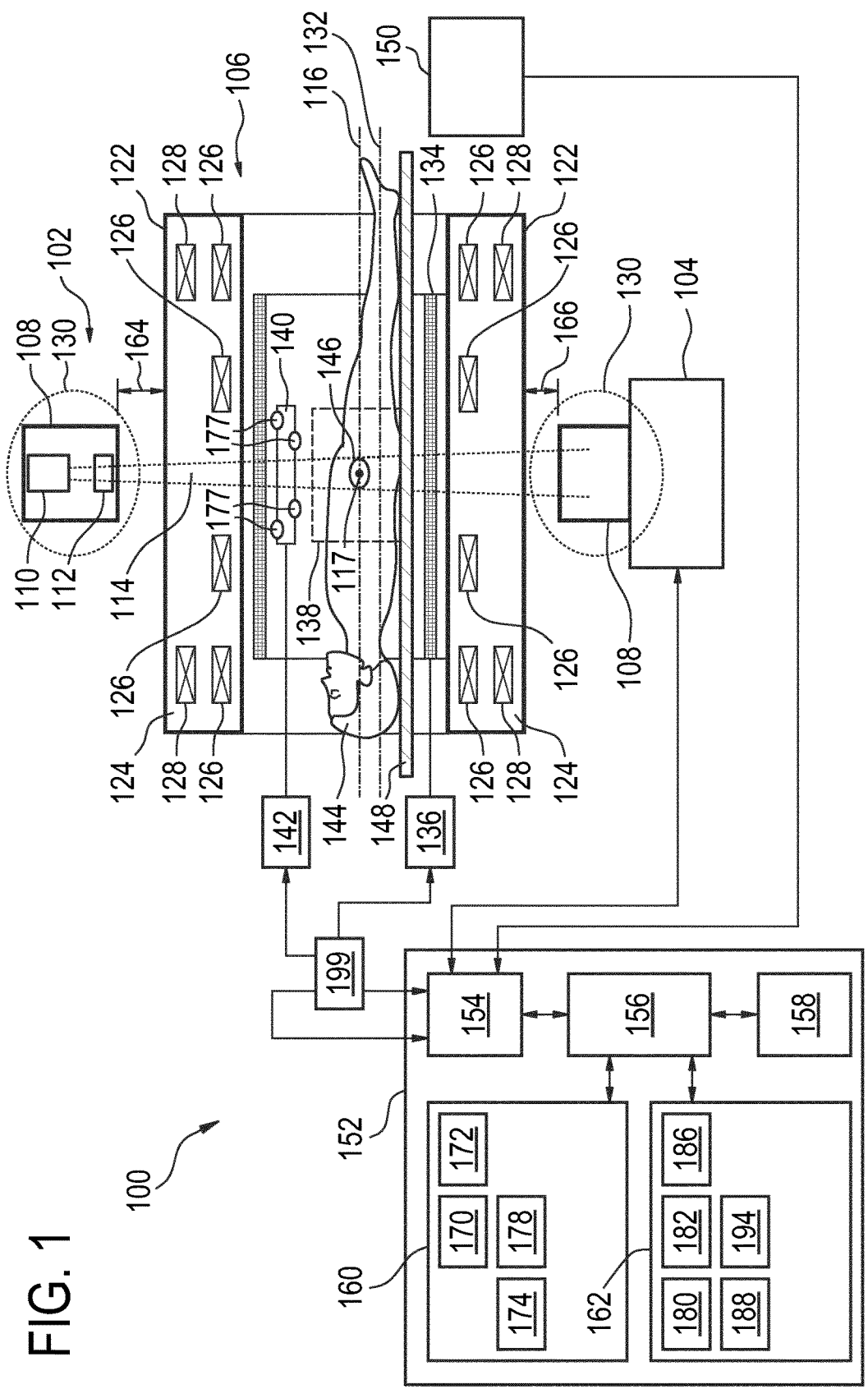
FIG. 1 shows a cross-sectional and functional view of a therapy system.

FIG. 1 shows a cross-sectional and functional view of a therapy system 100. The therapy system 100 is shown as comprising a radiotherapy apparatus 102 and a magnetic resonance imaging module 106. The radiotherapy apparatus 102 comprises a ring mechanism 108. The ring mechanism 108 supports a radiotherapy source 110. The radiotherapy source 110 is representative and may be a LINAC x-ray source, an x-ray 2 and a radioisotope gamma radiation source. Adjacent to the radiotherapy source 110 is a multi-leaf beam collimator 112 for collimating a radiation beam 114 that is generated by the radiotherapy source 110. The ring mechanism 108 is also adapted for moving e.g. rotating the radiotherapy source 110 and the beam collimator 112 about a rotational point 117 of the radiotherapy apparatus 102. A rotational axis 116 passes through the rotational point 117.

The magnetic resonance imaging module 106 is shown as comprising a main magnet 122. The ring mechanism 108 is ring-shaped and surrounds the main magnet 122. The main magnet 122 shown in FIG. 1 is a cylindrical type superconducting magnet. However, other magnets are also applicable for embodiments of the invention. The main magnet 122 has a supercooled cryostat 124. Inside the cryostat 124 there is a collection of superconducting coils 126. There are also compensation coils 128 whose current opposes the direction of current in the superconducting coils 126. This creates a low magnetic field zone 130 that circles or encompasses the main magnet 122. The cylindrical main magnet 122 is shown as having an axis 132 of symmetry.

Within the bore of the magnet there is a magnetic field gradient coil 134 which is used for acquisition of image magnetic resonance data to spatially encode objects within an imaging volume 138 of the main magnet 122. The magnetic field gradient coil 134 is connected to a magnetic field gradient coil power supply 136. The magnetic field gradient coil 134 is intended to be representative. Typically magnetic field gradient coils contain three separate sets of coils for spatially encoding in three orthogonal spatial directions. The imaging volume 138 is located in the center of the main magnet 122.

Adjacent to the imaging volume 138 is a radio frequency (RF) coil 140 for manipulating the orientations of magnetic spins within the imaging volume 138 and for receiving radio transmissions from spins also within the imaging volume 138. The radio frequency coil 140 is connected to a radio frequency transceiver 142. The radio frequency coil 140 and radio frequency transceiver 142 may be replaced by separate transmit and receive coils and a separate transmitter and receiver. It is understood that the radio frequency coil 140 and the radio frequency transceiver 142 are simply representative.

Within the center of the main magnet 122 is also located a subject 144. The subject 144 has a target volume 146 and is shown as reposing on a patient carrier 148. The RF coil 140 may transmit RF pulses into the target volume 146. The patient carrier 148 has a mechanical positioning system 150. The mechanical positioning system 150 is adapted for positioning the patient carrier 148 within the main magnet 122. Depending upon the space available inside of the main magnet 122, the mechanical positioning system 150 may move the patient carrier 148 in different directions including a direction perpendicular to the magnet axis 132. If there is more space available inside the main magnet 122 the mechanical positioning system 150 may have more degrees of freedom. For instance the mechanical positioning system 150 may position the patient carrier 148 with six degrees of freedom.

The radio frequency coil 140 may be connected to the patient carrier 148. The RF coil 140 is provided with a plurality of fiducial markers 177 that are configured for emitting magnetic resonance signals in response to RF pulse excitations.

The radio frequency transceiver 142, the magnetic field gradient coil power supply 136, the mechanical actuator 104, and the mechanical positioning system 150 are all shown as being connected to a hardware interface 154 of a computer system 152. The computer system 152 uses a processor 156 to control the therapy system 100, and to, for example, activate or control a spoiler 199 being for example an electronic switch to detune and tune the RF coil 140 and/or the magnetic field gradient coil 134. In another example, the spoiler 199 may wrap around each of at least part of the fiducial markers e.g., it may be a miniature solenoid coil around a fiducial marker (having a spherical shape).

The spoiler 199 may comprise an electronic switch which switches between open and closed states to detune and tune the RF coil 140 to a preselected resonance frequency. The electronic switch may comprise at least one field effect transistor (FET).

A spoiling element (e.g. spoiler) can be implemented by toggling a coil mode logical signal: when spoiling is in use, PIN current is routed through a coil, either to offset b0 field, or in split-mode, to generate a (time-varying) gradient over the marker volume. Routing can be implemented with FET switches. The coil can be a separate detuning coil, or a dedicated receive coil around the marker can be reused for spoiling purposes when receiving is not wanted.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the therapy system 100. The processor 156 is also connected to a user interface 158, computer storage 160, and computer memory 162. The radiotherapy apparatus 102 is not shown as being connected to the hardware interface 154. The radiotherapy apparatus 102 may be, for example, connected to the hardware interface 154 and communicates with the computer system 152 via the mechanical actuator 104.

For the example shown in FIG. 1, the rotational axis 116 of the radiotherapy apparatus is not coaxial with the magnet axis 132. The rotational point 117 is shown as being off center from the magnet axis 132. It can be seen that the target zone 146 is off-center and away from the magnet axis 132. The radiotherapy apparatus 102 has been moved by mechanical actuator 104 such that the rotational point 117 of the radiotherapy apparatus is within the target zone 146. It can be seen that the ring mechanism 108 has been moved relative to the magnet 122.

The radiation beam 114 passes through the rotational point 117. Placing the rotational point 117 at the center of the target zone 146 allows the target zone to be treated continuously when the radiation beam 114 is created by the radiotherapy source 110 and is rotated by the ring mechanism 108.

Computer storage 160 is shown as containing image magnetic resonance data 170 that have been acquired by the magnetic resonance imaging module 106. The computer storage 160 is shown as further containing diagnostic images (i.e. image representation) 172 that have been reconstructed from the image magnetic resonance data. The computer storage 160 is shown as further containing coordinates 174 of the target volume 146. The computer storage 160 is shown as further containing radiotherapy control signals 178.

The computer memory 162 contains machine executable instructions 180, 182, 186, 188, 194 for operation by the processor 156. The computer memory 162 is shown as containing a therapy system control module 180. The therapy system control module 180 contains machine executable instructions which allow the processor 156 to control the overall functioning of the therapy system 100. The computer memory 162 is shown as further containing a radiotherapy apparatus control module 182. The radiotherapy apparatus control module 182 contains machine executable instructions which allow the processor 156 to control the functioning of the radiotherapy apparatus 102.

The computer memory 162 is shown as further containing a magnetic resonance imaging control module 186. The magnetic resonance imaging control module 186 contains machine executable code which allows the processor 156 to control the functioning and operation of the magnetic resonance imaging module 106. The computer memory 162 is shown as further containing an image reconstruction module 188. The image reconstruction module 188 contains machine executable code which is used by the processor 156 to transform the image magnetic resonance data 170 into images 172.

The computer memory 162 is shown as further containing radiotherapy control signal generation module 194. The radiotherapy control signal generation module 194 contains computer executable code which the processor 156 uses to generate the radiotherapy control signals 178. The radiotherapy control signals 178 may be generated in conjunction with the coordinates 174 of the target volume 146.

The computer memory 162 further contains computer-executable code which enables the processor 156 to execute at least part of the below described method.

Figure 2:
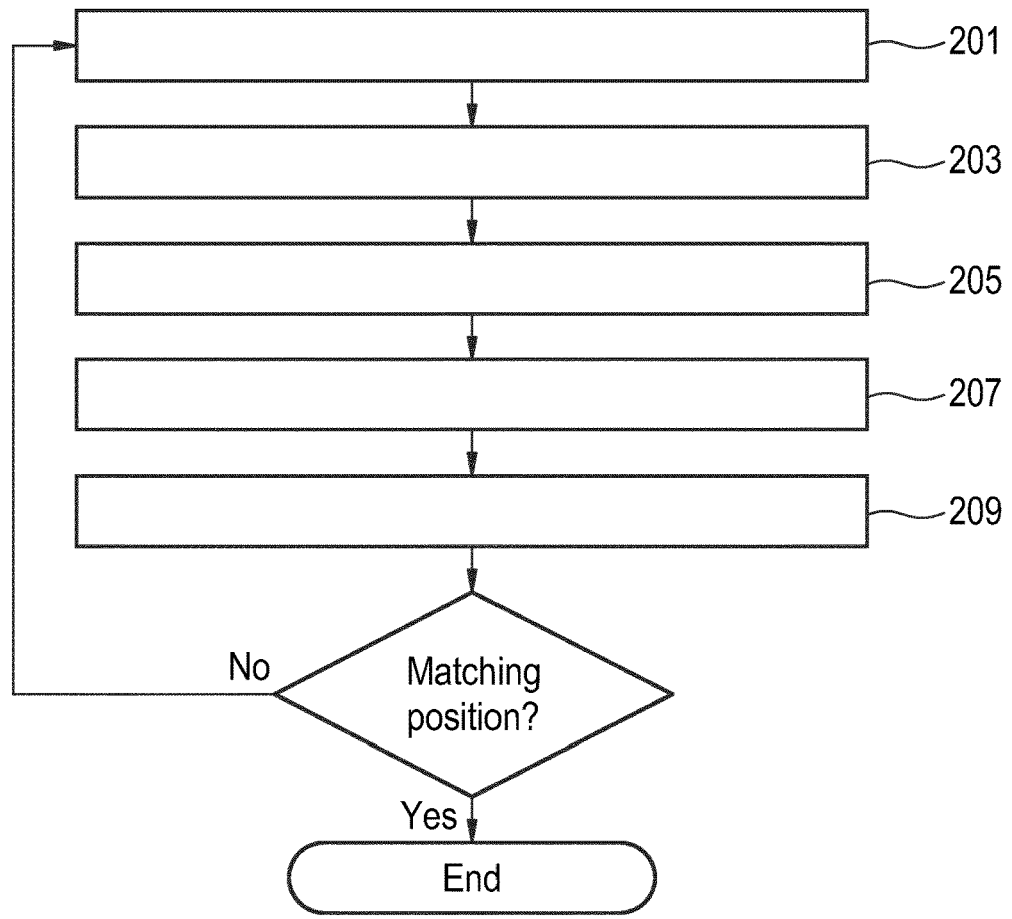
FIG. 2 is a flowchart of a method for a therapy procedure.

FIG. 2 is a flowchart of a method for positioning an RF coil e.g. 140 of a medical apparatus such as system 100 or part of system 100 comprising a magnetic resonance imaging module 106 comprising a main magnet 122 and a patient carrier 148. The RF coil 140 is connected to the patient carrier 148. The RF coil 140 is provided with a plurality of fiducial markers 177 that are configured for emitting magnetic resonance signals. The medical apparatus comprises a positioning system 150 for positioning the patient carrier 1148. The medical apparatus further comprises a memory 162 for storing machine executable instructions; and a processor 156. The medical apparatus may further comprise a spoiler 199 as described above.

The plurality of fiducial markers 177 may have non-ferromagnetic shells which define a spherical cavity filled with a liquid or gel compound that includes a F119 fluorine isotope. The spin lattice relaxation time of the Fluorine in the compound is preferably given a suitably small value (typically a few tens of milliseconds) by adding a paramagnetic substance to it, e.g. a small amount of $CuSO_4$ or $MnCl$. At 0.23 T, the resonant frequency of Fluorine is about 9.2 MHZ; and the proton resonant frequency is about 9.8 MHZ. The difference is great enough that the signals of resonating protons and resonating Fluorine can be differentiated. The resonance frequencies are sufficiently close that the same transmitter, receiver coils can be used to excite and receive the resonant signals of both resonating protons and resonating Fluorine. Alternately, a doubly tuned coil is tuned to both resonant frequencies.

At least one fiducial marker is larger than another of the plurality of fiducials for size-based differentiation. A size difference of 20% to 60% is preferred because that magnitude of size difference is readily detectable in a magnetic resonance image. The size difference allows looking at a reconstructed image of the fiducial markers to orient the image in reference to a priori knowledge of a positioning of the fiducial markers. For instance, when three fiducial markers are mounted on the RF coil 140, the differently sized fiducial marker can be mounted closest to the insertion end of the RF coil 140. A priori knowledge of the fiducial spacing, nearby anatomy, and the like can also be used to determine orientation. Alternately, the hollow cavities of the fiducial markers can have different shapes, such as crosses, cubes, and the like. Care should be taken to select shapes that remain unique and differentiable when projection images are taken along any direction. For example, the fiducial markers may be small spheres or cylinders couple of mm in size and may be incorporated to the rigid parts in the RF coil 140.

In step 201, the positioning system 150 is controlled to move the patient carrier 148 e.g. the positioning system 150 is controlled to continually move the patient carrier 148. The patient carrier 148 movement, in particular after determining an intermediate position of the RF coil 140, may take physical characteristics, such as the known acceleration/deceleration characteristics, into account. The movement can be in at least one direction.

In step 203, the MRI module may be controlled e.g. using the magnetic resonance imaging control module 186 to acquire MRI data responsive to excitation of magnetic resonance in at least a first set of the plurality of fiducial markers. For example, the RF coil 140 may be controlled to excite and receive the resonant signals of both resonating protons in the target volume and resonating Fluorine in the first set of fiducial markers.

In step 205, an image representation of the first set of fiducial markers may be reconstructed using the image reconstruction module 188 using the MRI data. As the resonance signals are spatially encoded by frequency and because the center frequencies of the fluorine and proton resonance spectra are shifted, the image reconstruction module 188 reconstructs the fiducial and proton images separately. Optionally, a frequency shift can be added to the fluorine signals to compensate for the difference in resonance frequencies.

The fiducial markers data is reconstructed by the image reconstruction module 188 and stored in the computer memory 162. The images of the subject may be stored in the computer memory 162 and can be overlaid or otherwise combined by the image reconstruction module 188 to produce a single image (e.g. the image representation of the first set of fiducial markers) showing the position of the first set of fiducial markers relative to selected portions of imaged anatomy. Optionally, images are reconstructed as two-dimensional projection images.

In step 207, the position of the RF coil 140 may be calculated using the position of the first set of fiducial markers in the reconstructed image.

The first set of fiducial markers may be detected from the reconstructed image by using e.g. cross-correlation with known marker shapes. For example, from the position of the first set of fiducial markers in the reconstructed image, a position calculator e.g. of the image reconstruction module 188 calculates the orientation and spatial location relative to the patient image of the RF coil 140. For example, the position calculator may monitor two or more fiducial markers of the first set of markers of a first size that are in a known relationship (e.g., aligned with) to an axis of the RF coil 140 to identify its orientation. Another identifiable fiducial or spacing among three or more fiducial markers of the first set of markers may be monitored to determine which way the RF coil 140 is facing or oriented along the axis. Similar monitoring of off-axis fiducials indicates rotational orientation of the RF coil 140. Finally, identifying a "center of mass," of the imaged first set of fiducial markers indicates a location of a corresponding point on the RF coil 140 along the identified axis. Other positioning algorithms may also be contemplated.

In step 209, the spoiler 199 may be controlled to suppress magnetic resonance signals emitted from one or more fiducial markers of the first set of fiducial markers based on the calculated position. For example, the position of the RF coil 140 may be calculated in at least one spatial direction. In case the calculated position matches the target position e.g. 117 along one spatial direction, suppressing magnetic resonance signals emitted from the fiducial marker used for the calculation of the position along the one spatial direction.

Steps 201)-209) may be repeated using a second set of fiducial markers of the plurality of fiducial markers as the first set of fiducial markers until the calculated position matches the predefined target position, wherein the second set of the fiducial markers comprises at least the first set of fiducial markers.

The final calculated position may be confirmed by imaging the patient carrier 148 in a stationary stage. After confirmation, any remaining fiducial marker that is still active or switched on may be switched off.

Figure 3:
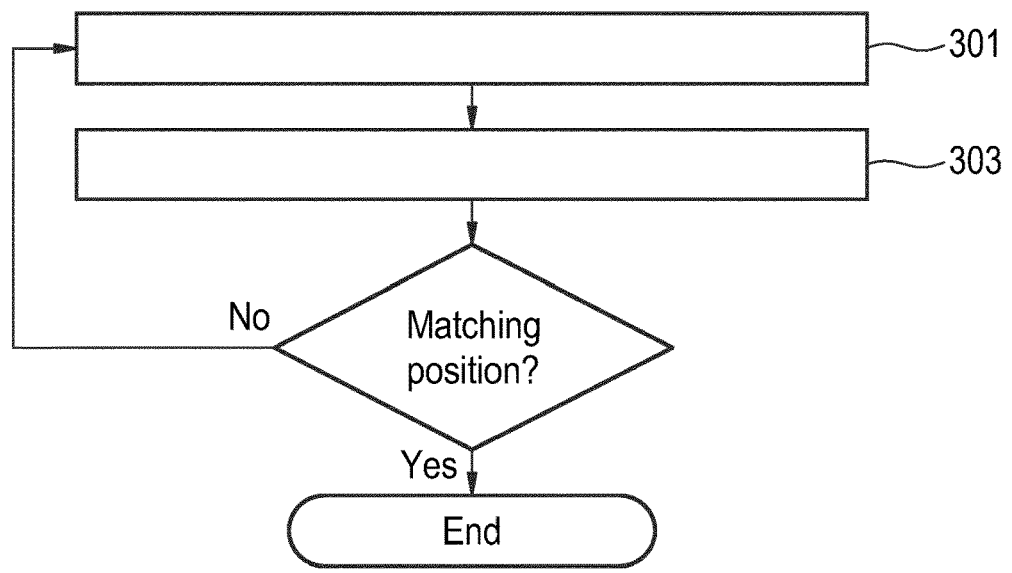
FIG. 3 is a flowchart of an alternative method for a therapy procedure.

FIG. 3 is a flowchart of an alternative method for positioning an RF coil e.g. 140 of a medical apparatus such as system 100 or part of system 100 comprising a magnetic resonance imaging module 106 comprising a main magnet 122 and a patient carrier 148. The RF coil 140 is connected to the patient carrier 148. The RF coil 140 is provided with a plurality of optical emitters that are configured to be tracked by optical systems such as one or more video cameras. The video camera may be located outside or inside the main magnet 122, or can be integrated to the RF coil 140. In addition, the video camera may be used in combination with additional optics, such as lenses, mirrors or optical fibers. The video camera may be preregistered to coincide with the physical structure of the RF coil 140 within the MR module and the resultant image. The video camera may have a line of sight to the optical emitters in order to detect the emitters. The medical apparatus further comprises a positioning system 150 for positioning the patient carrier 1148. The medical apparatus further comprises a memory 162 for storing machine executable instructions; and a processor 156.

In step 301, the positioning system 150 is controlled to move the patient carrier 148 e.g. the positioning system 150 is controlled to continuously move the patient carrier 148. The movement can be in at least one direction.

In step 303, the one or more video cameras may be controlled to calculate the position of the RF coil using. For example, the one or more video cameras may continually track the position of the optical (or light) emitters located on the RF coil 140. Images from the one or more video cameras may be used to triangulate positions of the light sources. And, the RF coil position may be measured. For example, when the RF coil 140 is placed on the patient carrier 148, the video camera is focused on the RF coil 122, and from the image taken by the video camera the analysis of the RF coil placement is performed e.g. at the position calculator of the image reconstruction module 188. Once the RF coil 140 is in the bore, the acquired position data may be used to adjust patient carrier position.

Steps 301-303 may be repeated until the calculated position matches a predefined target position e.g. 117.

In an alternative embodiment, the position of the RF coil may be determined using a combination of the method step 303 and steps 203-207 (e.g. step 207 may further comprise step 303). In this case, the RF coil 140 may be provided with the plurality of optical emitters as well as the plurality of fiducial markers. For example, the position determined in step 303 may be used as a cross check of the position determined in steps 203-207, wherein the repetition of steps 201)-209) is performed until both determined positions match the predefined target position. This may further increase the accuracy of the positioning and of the therapy procedure as described above.

In an alternative embodiment, the position of the RF coil 140 may be first (or initially) determined using the method of the fiducial markers as described above e.g. steps 203-207 until the calculated position of the RF coil reaches a predefined position at which the radiation level is at a maximum allowed radiation level beyond which the fiducial markers cannot be reliably used. After reaching that predefined position the video camera may be used as described in step 303 instead of the method of the fiducial markers to calculate the position of the RF coil until the calculated position matches the final target position. This may further increase the accuracy of the positioning and of the therapy procedure as described above.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus.

Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

LIST OF REFERENCE NUMERALS 100 therapy system
102 radiotherapy apparatus
104 mechanical actuator
106 magnetic resonance imaging module
108 ring mechanism
110 radio therapy source
112 multi-leaf beam collimator
114 radiation beam
116 rotational axis
117 rotational point
122 main magnet
124 cryostat
126 superconducting coil
128 compensation coil
130 low magnetic field zone
132 magnet axis
134 magnetic field gradient coil
136 magnetic field gradient coil power supply
138 imaging volume
140 radio frequency coil
142 radio frequency transceiver
144 subject
146 target volume
148 patient carrier
150 mechanical positioning system
152 computer system
154 hardware interface
156 processor
158 user interface
160 computer storage
162 computer memory
164 top distance
166 bottom distance
170 image magnet resonance data
172 diagnostic images
174 coordinates of target volume
177 fiducial markers
178 radio therapy control signals
180 therapeutic apparatus control module
182 radio therapy apparatus control module
186 magnetic resonance imaging control module
188 image reconstruction module
194 radio therapy control signal generation module
199 spoiler.

The invention claimed is:

1. A therapy system comprising:
a magnetic resonance imaging module comprising a main magnet and a patient carrier configured to move into or out of an examination zone within the main magnet;
a radiotherapy device configured to deliver and direct a radiotherapy beam along an axis to a predefined target position in the examination zone;
a RF coil connected to the patient carrier, wherein the RF coil is provided with a plurality of fiducial markers that are configured for emitting magnetic resonance signals;
a positioning system for positioning the patient carrier;
a spoiler to suppress magnetic resonance signals emitted from one or more fiducial markers;
a memory for storing machine executable instructions; and a processor, wherein execution of the machine executable instructions causes the processor to:
  a. control the positioning system to move the patient carrier;
  b. control the MRI module to acquire MRI data responsive to excitation of magnetic resonance in at least a first set of the plurality of fiducial markers;
  c. reconstruct using the MRI data an image representation of the first set of fiducial markers;
  d. calculate the position of the RF coil using the position of the first set of fiducial markers in the reconstructed image;
  e. control the spoiler to suppress magnetic resonance signals emitted from one or more fiducial markers of the first set of fiducial markers in dependence of the calculated position relative to the predefined target position;
  f. repeating steps a)-e) using a second set of fiducial markers of the plurality of the fiducial markers as the first set of fiducial markers until the calculated position matches the predefined target position, wherein the second set of the fiducial markers comprises at least the first set of fiducial markers.

2. The therapy system of claim 1, wherein matching the calculated position with the target position in step f) comprises:
  comparing the distance between the calculated position and the target position with a predefined minimum matching distance threshold value;
  in response to a determination that the distance is smaller than the predefined minimum matching distance threshold value, determining the radiation level at the calculated position;
  in response to a determination that the radiation level is higher than a predetermined maximum allowed radiation level, redefining the minimum matching distance threshold value and repeating steps a-e) using the redefined minimum matching distance threshold value.

3. The therapy system of claim 1, wherein the position of the RF coil is calculated in at least one spatial direction, wherein in case the calculated position matches the target position along one spatial direction, suppressing of magnetic resonance signals emitted from the fiducial marker used for the calculation of the position along the one spatial direction.

4. The therapy system of claim 1, wherein in case the calculated position matches the target position, suppressing comprises determining artifact regions in the MRI data and suppressing magnetic resonance signals emitted from fiducial markers that correspond to the artifact regions.

5. A medical apparatus comprising:
  a magnetic resonance module comprising a main magnet and a patient carrier configured to move into or out of an examination zone within the main magnet;
  a RF coil connected to the patient carrier, wherein the RF coil is provided with a plurality of fiducial markers that are configured for emitting magnetic resonance signals;
  a positioning system for positioning the patient carrier;
  a spoiler to suppress magnetic resonance signals emitted from one or more fiducial markers;
  a memory for storing machine executable instructions; and
  a processors, wherein execution of the machine executable instructions causes the processor to:
  a. control the positioning system to move the patient carrier;
  b. control the MRI module to acquire MRI data responsive to excitation of magnetic resonance in at least a first set of the plurality of fiducial markers;
  c. reconstruct using the MRI data an image representation of the first set of fiducial markers;
  d. calculate the position of the RF coil using the position of the first set of fiducial markers in the reconstructed image;
  e. control the spoiler to suppress magnetic resonance signals emitted from one or more fiducial markers of the first set of fiducial markers based on the calculated position relative to a predefined target position;
  f. repeating steps a)-e) using a second set of fiducial markers of the plurality of the fiducial markers as the first set of fiducial markers until the calculated position matches the predefined target position, wherein the second set of the fiducial markers comprises at least the first set of fiducial markers.

6. The medical apparatus of claim 5, further comprising a radiotherapy device configured to deliver and direct a radiotherapy beam along an axis to the predefined target position in the imagine zone.

7. The medical apparatus of claim 5, wherein matching the calculated position with the target position in step f) comprises:
  comparing the distance between the calculated position and the target position with a predefined minimum matching distance threshold value;
  in response to a determination that the distance is smaller than the predefined minimum matching distance threshold value, determining the radiation level at the calculated position;
  in response to a determination that the radiation level is higher than a predetermined maximum allowed radiation level, redefining the minimum matching distance threshold value and repeating steps a-e) using the redefined minimum matching distance threshold value.

8. The medical apparatus of claim 1, step a) further comprising control the positioning system to stop the patient carrier at a predefined stopping time, wherein the repeating of steps a)-e) results in one or more iterations, wherein the predefined stopping time for a given iteration is determined using the calculated position in the previous iteration.

9. The method of claim 5, wherein repeating of steps a)-e) results in one or more iterations, wherein the MRI module is controlled to acquire the MRI data with an increasing spatial accuracy with the number of iterations.

10. The medical apparatus of claim 5, wherein the fiducial markers include dipoles, wherein suppressing the magnetic resonance signals emitted from the fiducial markers comprises applying at least one of an RF spoiling and gradient spoiling.

11. The method of claim 5, comprising calculating the position of the RF coil in at least one spatial direction, wherein in case the calculated position matches the target position along one spatial direction, suppressing emission of magnetic resonance signals from the fiducial marker used for the calculation of the position along the one spatial direction.

12. The medical apparatus of claim 5, wherein in case the calculated position matches the target position, suppressing comprises determining artifact regions in the MRI data and suppressing magnetic resonance signals emitted from fiducial markers that correspond to the artifact regions.

13. The medical apparatus of claim 12, wherein the suppression of the magnetic resonance signals emitted from a fiducial marker is performed if the artifact level of the corresponding artifact region is higher than a predefined artifact level.

14. A method of controlling a medical apparatus, the medical apparatus comprising a magnetic resonance imaging module comprising a main magnet and a patient carrier configured to move into or out of an examination zone within the main magnet; a RF coil connected to the patient carrier, wherein the RF coil is provided with a plurality of fiducial markers that are configured for emitting magnetic resonance signals; a positioning system for positioning the patient carrier; and a spoiler: the method comprises:
   a. control the positioning system to move the patient carrier;
   b. control the MRI module to acquire MRI data responsive to excitation of magnetic resonance in at least a first set of the plurality of fiducial markers;
   c. reconstruct using the MRI data an image representation of the first set of fiducial markers;
   d. calculate the position of the RF coil using the position of the first set of fiducial markers in the reconstructed image;
   e. control the spoiler to suppress magnetic resonance signals emitted from one or more fiducial markers of the first set of fiducial markers based on the calculated position;
   f. repeating steps a)-e) using a second set of fiducial markers of the plurality of the fiducial markers as the first set of fiducial markers until the calculated position matches a predefined target position, wherein the second set of the fiducial markers comprises at least the first set of fiducial markers.

15. A computer program product comprising computer executable instructions to perform the method steps of the method of claim 14.

* * * * *